(12) United States Patent
Huang et al.

(10) Patent No.: US 6,920,790 B2
(45) Date of Patent: Jul. 26, 2005

(54) APPARATUS FOR IN-SITU NONDESTRUCTIVE MEASUREMENT OF YOUNG'S MODULUS OF PLATE STRUCTURES

(75) Inventors: Jerry Qixin Huang, Hacienda Heights, CA (US); Robert J. Perez, Westminster, CA (US); Leo M. DeLangis, Huntington Beach, CA (US)

(73) Assignee: The Boeing Company, Chicago, IL (US)

( * ) Notice: Subject to any disclaimer, the term of this patent is extended or adjusted under 35 U.S.C. 154(b) by 225 days.

(21) Appl. No.: 10/422,437

(22) Filed: Apr. 24, 2003

(65) Prior Publication Data

US 2003/0233876 A1 Dec. 25, 2003

Related U.S. Application Data

(63) Continuation-in-part of application No. 09/602,173, filed on Jun. 22, 2000, now Pat. No. 6,575,036.

(51) Int. Cl.$^7$ .............................................. G01N 29/18
(52) U.S. Cl. .............................. 73/597; 73/602; 73/644
(58) Field of Search .......................... 73/597, 602, 644, 73/598, 609, 509, 587, 629, 618, 620, 633, 599

(56) References Cited

U.S. PATENT DOCUMENTS

| | | | |
|---|---|---|---|
| 3,720,098 A | 3/1973 | Dixon | |
| 4,307,616 A | 12/1981 | Vasile | |
| 4,457,174 A | 7/1984 | Bar-Cohen et al. | |
| 4,562,736 A | 1/1986 | Iwasaki et al. | |
| 4,688,429 A | 8/1987 | Holroyd | |
| 4,845,989 A | 7/1989 | Titlow et al. | |
| 5,031,457 A | 7/1991 | Kline | |
| 5,033,304 A | 7/1991 | Rosen | |
| 5,127,268 A | 7/1992 | Klineq | |
| 5,154,081 A | 10/1992 | Thompson et al. | |
| 5,251,486 A | 10/1993 | Thompson et al. | |
| 5,369,997 A | 12/1994 | Roberts et al. | |
| 5,408,882 A | 4/1995 | McKinley et al. | |
| 5,456,114 A | 10/1995 | Liu et al. | |
| 5,533,399 A | 7/1996 | Gibson et al. | |
| 5,578,757 A | 11/1996 | Roth | |
| 5,741,971 A | 4/1998 | Lacy | |
| 5,804,727 A | 9/1998 | Lu et al. | |
| 5,929,315 A | 7/1999 | Dunegan | |
| 6,053,034 A | 4/2000 | Tsui et al. | |
| 6,062,083 A | 5/2000 | Dunegan | |
| 6,092,421 A | 7/2000 | Bar-Cohen et al. | |
| 6,173,613 B1 | 1/2001 | Dunegan | |
| 6,575,036 B1 * | 6/2003 | Huang et al. | ................. 73/597 |

* cited by examiner

*Primary Examiner*—Hezron Williams
*Assistant Examiner*—Jacques M. Saint-Surin
(74) *Attorney, Agent, or Firm*—Alston & Bird LLP

(57) ABSTRACT

A method and apparatus for determining stiffness of a plate-like structure including a monolithic or composite laminate plate entails disposing a device for generating an acoustical pulse against a surface of the plate and disposing a detecting device against the same surface spaced a known distance from the pulse-generating device, and using the pulse-generating device to emit a pulse so as to create an extensional wave in the plate. The detecting device is used to determine a time of flight of the wave over the known distance, and the wave velocity is calculated. A Young's modulus of the plate is determined by a processor based on the wave velocity. Methods and apparatus for evaluating both isotropic plates and anisotropic laminates are disclosed.

20 Claims, 4 Drawing Sheets

APPARATUS FOR IN-SITU NONDESTRUCTIVE MEASUREMENT OF YOUNG'S MODULUS OF PLATE STRUCTURES

RELATED APPLICATION(S)

The present application is a continuation-in-part of U.S. patent application Ser. No. 09/602,173 filed Jun. 22, 2000, now U.S. Pat. No. 6,575,036, the contents of which are incorporated herein in their entirety.

STATEMENT REGARDING FEDERALLY SPONSORED RESEARCH OR DEVELOPMENT

The invention described herein was made in the performance of work under NASA Cooperative Agreement NCC8-39 and is subject to the provisions of Section 305 of the National Aeronautics and Space Act of 1958 (42 U.S.C. 2457).

FIELD OF THE INVENTION

The invention relates to nondestructive test methods and apparatus for determining stiffness properties of plate structures. The invention relates more particularly to such methods and apparatus employing propagation of acoustic waves through a plate structure of homogeneous or composite laminate form for determining Young's modulus of the plate structure.

BACKGROUND OF THE INVENTION

In a variety of mechanical or structural devices or assemblies including, for example, aircraft, spacecraft and other types of vehicles or vessels; buildings; bridges and other structures, it is frequently desired to be able to determine changes in material properties of a given part, because such changes can be indicative of degradation of the part. For example, material stiffness is an important parameter affecting the performance of a structure. While structures are typically designed based on a known initial stiffness of the materials making up the structure, various factors can cause the materials to lose stiffness. Stress, fatigue, and environmental attack such as thermal and/or oxidation processes are just a few of the mechanisms by which a material can be degraded in terms of material stiffness. Fiber/matrix composite materials are particularly susceptible to stiffness degradation, chiefly through a process known as micro-cracking in which microscopic cracks develop in the matrix material that binds the fibers together. Such micro-cracking can cause deleterious changes in mechanical properties, stress concentration, and redistribution within the composite material, which in turn can lead to performance degradation, delamination, and fiber damage. It is difficult, however, to detect micro-cracking using the types of nondestructive testing methods that heretofore have been available.

Prior to the present invention, there was no known nondestructive testing device suitable for use in the field, such as a hand-held device, for quantitatively determining changes in stiffness of a plate such as a composite laminate plate along an in-plane direction of the plate. The prior art teaches various methods for determining stiffness of isotropic materials using ultrasonic wave propagation through the material. For example, U.S. Pat. No. 5,741,971 to Lacy discloses a method for nondestructively measuring a Young's modulus of a bulk isotropic material, such as cements or completion gels used in the petroleum industry for interzone isolation and fracture containment in drilling operations. The method involves using the through-transmission technique in which an ultrasonic transducer is disposed adjacent one end of a sample slug of the bulk material and another ultrasonic transducer is disposed adjacent an opposite end of the sample. The length of the sample between the two transducers is known. An ultrasonic pulse is generated by one of the transducers so as to cause an ultrasonic compression or longitudinal wave to be propagated beginning at one end of the sample, and the other transducer detects the wave when it arrives at the opposite end of the sample. The elapsed time between initiation of the wave at one end of the sample and arrival of the wave at the other end of the sample is measured. Based on this time and the known length of the sample, a velocity of the wave through the sample is calculated. A Young's modulus for the material is then calculated based on the wave velocity and the known density and Poisson's ratio of the material. The method of Lacy and the theory behind it are applicable only to isotropic materials. Lacy's method requires placing transducers on two opposite sides of the sample, and thus would be difficult to apply to in-situ testing of a structure where it may be difficult or impossible to access both sides of the structure. Even if both sides of the structure could be accessed, the through-transmission technique of Lacy still cannot give a measurement of Young's modulus in an in-plane direction, but can only provide an indication of stiffness in the thickness direction, which is the less interesting of the two directions.

U.S. Pat. No. 5,154,081 to Thompson et al. discloses a method for ultrasonic measurement of material properties for metal plates, involving using two transducers and a receiver arranged non-colinearly on one side of the plate. The two transducers generate Lamb waves that propagate along two different directions to the receiver. Based on differences in calculated velocities of the two Lamb waves, Thompson deduces material properties such as grain orientation and stress. The method is applicable only to metals, and does not provide a material stiffness measurement.

There has been a need, therefore, for a nondestructive method and apparatus for measuring in-plane stiffness properties of plates including homogeneous isotropic plates and composite laminate plates. Additionally, there has been a need for such a method and apparatus that can be used for in-situ examination of a plate where it may not be possible to access both sides of the plate.

SUMMARY OF THE INVENTION

The above needs are met and other advantages are achieved by the present invention, which provides a method and apparatus for quantitatively evaluating in-plane stiffness properties of a plate in a nondestructive manner that is applicable to in-situ use, necessitating access to only one side of the plate. The apparatus comprises a transducer for imparting energy to the plate at a first point located on a first of the major surfaces of the plate so as to cause an elastic wave to originate at the first point and propagate along the plate as a plate wave or guided wave. The plate wave generally consists of two wave modes, i.e., extensional and flexural wave modes. At a second point on the same surface of the plate and spaced from the first point along an in-plane direction, the extensional-mode wave, which travels faster than the flexural wave, is detected by a sensor when it arrives. A velocity of the extensional wave along the in-plane direction of the plate is determined by a processor. Based on this velocity, a material stiffness of the plate along the in-plane direction is calculated by the processor.

The wave velocity can be determined by the processor based upon the distance d between the first and second points by measuring the elapsed time t required for the extensional-mode wave to travel the distance d from the first point to the second point, and dividing the distance d by the time t. Based on the velocity, a stiffness parameter for the plate along the in-plane direction is determined by the processor. The determination of the stiffness parameter is based on elastic wave propagation. The apparatus can be applied to both homogeneous isotropic plates and composite laminate plate structures.

In accordance with a preferred embodiment of the invention applicable particularly to homogeneous isotropic plates, the stiffness parameter calculation in accordance with the invention is performed by the processor by calculating the Young's modulus based on the distance d and the time t. More particularly, the Young's modulus E is calculated by the processor based on the equation $$E=(1-v^2)\rho(d/t)^2,$$

where v is a predetermined Poisson's ratio for the material of the plate and $\rho$ is a predetermined density of the material of the plate.

Preferably, the elastic wave is generated by a transducer in acoustical communication with the plate that applies acoustic energy to the plate. For example, a device for emitting acoustic pulses can be disposed against the plate surface and activated to create an acoustic pulse. An ultrasonic transducer or acoustic emission sensor can be used for this purpose. The extensional wave mode is detected with a second sensor placed a known distance from the first sensor against the same surface of the plate and in acoustical communication therewith. It will thus be appreciated that unlike prior art methods employing the through-transmission technique in which a longitudinal wave is propagated from one side of a material to the other, the apparatus of the invention is suitable for in-situ applications where it may not be possible or practical to locate sensors on both sides of the structure. For example, the apparatus and method of the present invention may advantageously be utilized to inspect the skin or other portions of the structural assembly of an aircraft that may only be readily accessible from one side thereof.

The embodiments of the apparatus described above are applicable primarily to isotropic plates and to quasi-isotropic composite laminate plates in which the plies are arranged in a lay-up such that the resulting laminate exhibits isotropic elastic behavior in the plane of the plate. The invention also provides an apparatus for determining Young's moduli of a composite laminate plate in the more general case of anisotropic laminates. This embodiment of the apparatus involves the processor solving a set of simultaneous equations to determine Young's moduli for the plate along two orthogonal in-plane x- and y-directions corresponding to the zero-degree and 90-degree fiber directions of the laminate. The equations relate the Young's moduli to the extensional wave velocities along these directions and to Poisson's ratios and in-plane stiffness parameters for the plate. More specifically, one embodiment of the invention includes a processor adapted to determine extensional wave velocities $C_x$ and $C_y$ along the x- and y-directions of a composite laminate plate, and then to solve the set of equations:

$$C_x=\sqrt{A_{11}/\rho h} \qquad \text{Eq. (1)}$$

$$C_y=\sqrt{A_{22}/\rho h} \qquad \text{Eq. (2)}$$

$$E_{xx} = \frac{\sigma_{xx}}{\epsilon_{xx}^\circ} = \frac{A_{11}A_{22} - A_{12}^2}{hA_{22}} \qquad \text{Eq. (3)}$$

$$v_{xy} = -\frac{\epsilon_{yy}^\circ}{\epsilon_{xx}^\circ} = \frac{A_{12}}{A_{22}} \qquad \text{Eq. (4)}$$

$$E_{yy} = \frac{A_{11}A_{22} - A_{12}^2}{hA_{11}} \qquad \text{Eq. (5)}$$

$$v_{yx} = \frac{A_{12}}{A_{11}} \qquad \text{Eq. (6)}$$

where h is the plate thickness, $A_{ij}$ (i,j=1 and 2) are the in-plane stiffnesses of the plate as defined in the composite laminate theory, $\rho$ is the plate density, and $v_{xy}$ and $v_{yx}$ are Poisson's ratios for the plate along the x- and y-directions. The plate density and Poisson's ratios will generally be known or can readily be determined. Thus, these equations can be solved for the Young's moduli. It can be shown, for quasi-isotropic composite plates, that this set of equations can be greatly simplified and reduced to the equation $$E=(1-v^2)\rho(d/t)^2$$

set forth above.

The invention also provides an apparatus for quantitatively determining a change in Young's modulus for a plate. This embodiment of the apparatus comprises a transducer for imparting energy to the plate so as to cause respective extensional-mode waves to originate and propagate along the plate in the in-plate direction, and a sensor for detecting the arrival of the respective extensional-mode waves. The transducer and the sensor are spaced apart by a predetermined distance d. The apparatus of this embodiment also includes a processor for determining the elapsed time t required for the extensional-mode wave to travel the predetermined distance d, and for calculating Young's modulus E. Thus, a set of baseline data, t and E, can be obtained during this first test and denoted as $t_1$ and $E_1$. Following a period of time, such as following a period of service, Young's modulus may again be determined by performing a second test in the same manner by determining the elapsed time $t_2$ for the extensional mode wave to travel the predetermined distance d, and to calculate Young's modulus $E_2$. A change in Young's modulus for the plate is calculated by the processor based on a degree of difference of the times $t_1$ and $t_2$. More particularly, it is assumed that the density and Poisson's ratio for the material of the plate are constant or their change is negligible between the two different times at which the first and second tests are performed. A ratio of Young's moduli measured during the two tests is calculated by the processor based on a ratio of the times $t_1$ and $t_2$. Advantageously, the ratio of Young's moduli is calculated by the processor in accordance with the equation $$E_2/E_1=(t_1/t_2)^2,$$

where $E_1$ is Young's modulus for the first test and $E_2$ is Young's modulus for the second test. The first and second tests may be conducted at two different times, in which case the change in Young's modulus represents a change in material stiffness over time. Thus, the apparatus of this embodiment of the invention can be used for periodic inspection as a way of monitoring the health of a structure, such as an aircraft or the like. The information regarding changes in material stiffness can be used for prediction of remaining life of the structure or other purposes.

BRIEF DESCRIPTION OF THE DRAWINGS

The above and other objects, features, and advantages of the invention will become more apparent from the following description of certain preferred embodiments thereof, when taken in conjunction with the accompanying drawings in which.

DETAILED DESCRIPTION OF THE DRAWINGS

Figure 1:
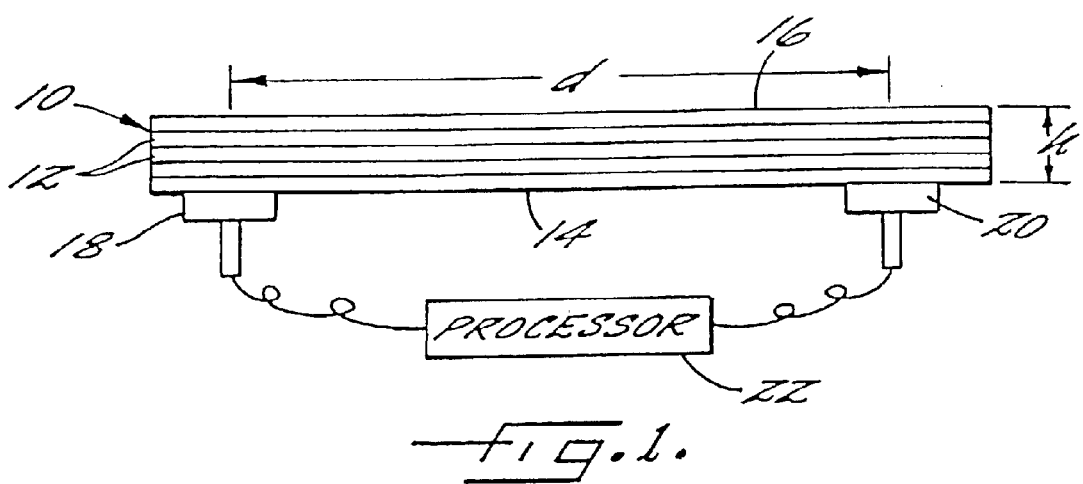
FIG. 1 is a schematic depiction of a testing apparatus positioned on a plate structure for measuring a time of flight of an extensional wave along the plate in accordance with a method of the invention.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

The present invention is premised on a unique application of the theory of extensional wave behavior in plate structures and the composite laminate theory. It is known from theoretical work on wave behavior in composite laminate plates that for symmetric and orthotropic laminate plates, the extensional wave velocity in the x-direction (i.e., along the 0° ply direction) is given by $$C_x = \sqrt{A_{11}/\rho h} \qquad \text{Eq. (1)}$$

where $A_{11}$ is the in-plane stiffness in the x-direction, $\rho$ is the plate density, and h is the plate thickness. Similarly, the extensional wave velocity in the y-direction (along the 90° ply direction) is given by $$C_y = \sqrt{A_{22}/\rho h} \qquad \text{Eq. (2)}$$

where $A_{22}$ is the in-plane stiffness in the y-direction. By symmetric laminate is meant a laminate in which the plies are arranged so as to be symmetric about a central plane dividing the plate thickness in half, and in which for every ply of +θ orientation there is an identical ply of −θ orientation. Such a ply lay-up is also commonly referred to as a balanced symmetric ply lay-up.

It is also known that for a balanced symmetric laminate, the Young's modulus in the x-direction is given by $$E_{xx} = \frac{\sigma_{xx}}{\epsilon_{xx}^o} = \frac{A_{11}A_{22} - A_{12}^2}{hA_{22}} \qquad \text{Eq. (3)}$$

and the Poisson's ratio is given by $$v_{xy} = -\frac{\epsilon_{yy}^o}{\epsilon_{xx}^o} = \frac{A_{12}}{A_{22}} \qquad \text{Eq. (4)}$$

Similarly, the Young's modulus in the y-direction is $$E_{yy} = \frac{A_{11}A_{22} - A_{12}^2}{hA_{11}} \qquad \text{Eq. (5)}$$

and the Poisson's ratio is $$v_{yx} = \frac{A_{12}}{A_{11}} \qquad \text{Eq. (6)}$$

The Poisson's ratios $v_{xy}$ and $v_{yx}$ are material constants and can be determined by mechanical methods or can be calculated from the lamina (single ply) data. Likewise, the density $\rho$ is a material constant and can readily be determined. Thus, Equations (1) through (6) represent a set of six simultaneous equations having seven unknowns, namely, $c_x$, $c_y$, $A_{11}$, $A_{22}$, $A_{12}$, $E_{xx}$, and $E_{yy}$. However, consider the situation where the extensional velocites $c_x$ and $c_y$ are known. Then, the equations can be solved to determine the Young's moduli $E_{xx}$ and $E_{yy}$. In other words, the Young's modulus along a defined direction of a plate can be determined if the extensional wave velocity along that direction is known.

The extensional velocity along a defined direction of a plate can be experimentally determined by causing an extensional wave to propagate along the plate and measuring the time of flight required for the wave to travel a known distance along the plate. The quantitative stiffness determination of the present invention is applicable primarily to thin plates in which the thickness of the plate is much smaller than the length and width dimensions of the plate. Qualitative results may be obtained, however, even for non-plate structures using the same methodology as that described herein. It is anticipated that quantitative results could even be obtained for non-plate structures by using empirically derived correction factors.

FIG. 1 schematically depicts a testing apparatus that can suitably be used for initiating an extensional wave and measuring a time of flight. A composite laminate plate 10 is schematically depicted as composed of a plurality of plies 12 laid atop one another. FIG. 1 is a view looking-at the plate edgewise. The major surfaces 14 and 16 of the plate define a plate thickness h therebetween.

Figure 2:
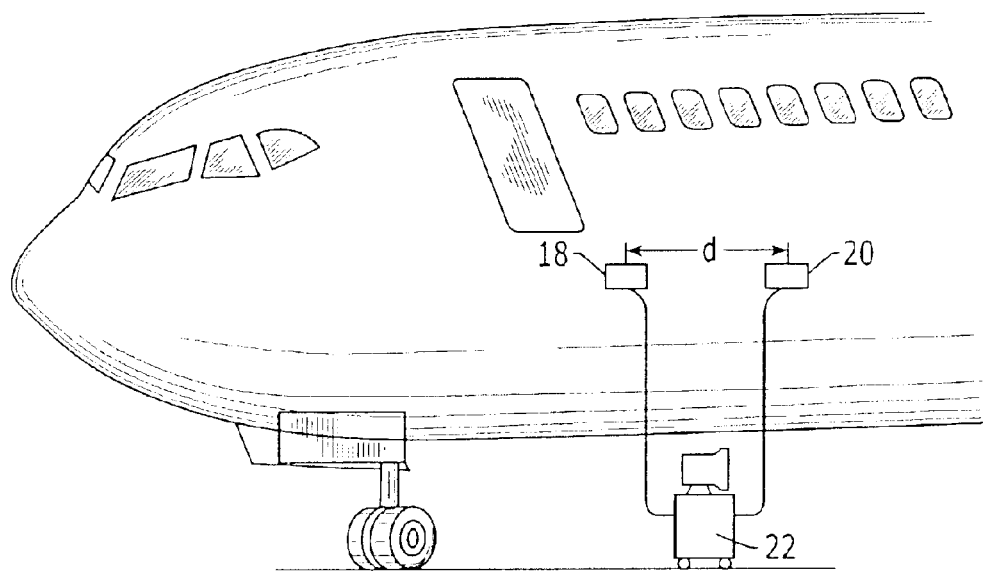
FIG. 2 is a perspective view of an aircraft that is undergoing an evaluation with a testing apparatus in accordance with an embodiment of the invention.

The testing apparatus and method of the present invention can be utilized to determine changes in the material properties of a variety of mechanical or structural devices or assemblies. As shown in FIG. 2, the testing apparatus and method may be utilized to determine changes in the material properties of the composite laminate plate(s) that form the skin or other portions of the structural assembly of an aircraft. Similarly, the testing apparatus and method may be employed to inspect the skin or other portions of the structural assembly of a spacecraft, a marine vessel, an automobile or other vehicle or vessel. Additionally, the testing apparatus and method may be employed to inspect other structures such as buildings, bridges or the like.

In accordance with a preferred embodiment of the invention, a pair of sensors 18 and 20 are disposed against one of the major surfaces of the plate, such as the surface 14 as shown in FIGS. 1 and 2, so as to be in acoustical communication therewith. The sensors 18 and 20 can be permanently bonded on or embedded in the structure, or the sensors may be configured as respective hand-held devices. The sensors 18 and 20 each comprises a device for converting an electrical pulse into an acoustical pulse or signal and vice versa, such as a 50 kHz to 2 MHz ultrasonic transducer or acoustic emission sensor. The sensor 18 is connected to a suitable processor 22, such as via wire or wireless connection to a microprocessor or other computing device, which provides an electrical pulse to the sensor 18 and receives a signal from the sensor 18 indicating that an acoustical pulse has been initiated. The processor 22 includes a clock that begins measuring an elapsed time upon receipt of this signal in a proper sampling rate according to the accuracy required for the modulus measurements, in a range of above 5 MHz. The time required for the extensional wave to travel between the two sensors 18 and 20 is equal to the sensor spacing d divided by the sound velocity c. Thus, as an example of determining the proper sampling rate, consider a case in which the sensor spacing d is 0.05 m and the material's velocity of sound propagation c is 6000 m/s. Accordingly, to observe a two percent change in modulus, a minimum sampling rate of about 10 MHz would be required. The higher the sampling rate, the smaller the change in modulus that can be measured.

Upon activation of the sensor 18, an extensional wave will begin to be propagated through the plate 10. After an elapsed time t measured from when the sensor 18 is activated, the extensional wave will arrive at the location of the second sensor 20. Upon detection of the wave, the second sensor 20 sends a signal to the processor 22, and the elapsed time between initiation of the acoustical pulse at the first sensor location and arrival of the extensional wave at the second sensor location is determined by the processor 22. The distance d between the sensors 18 and 20 is known. Accordingly, an extensional wave velocity can be determined by the processor or another associated computing device, such as a personal computer, a server or the like (hereinafter collectively termed "the processor") by dividing the distance d by the elapsed time t.

The wave velocity determined in this manner is the velocity along a particular direction of the plate 10 defined by the orientation of the sensors 18, 20 with respect to each other. In the general case of an anisotropic composite laminate, the in-plane stiffnesses $A_{11}$ and $A_{22}$ in the x- and y-directions are different, and thus the extensional wave velocities are different in different directions, as indicated by Equations (1) and (2) above. Examination of Equations (3) and (5) also reveals that the Young's moduli are different in the x- and y-directions. The present invention provides a method and an associated apparatus including a processor 22 for determining the Young's moduli along the x- and y-directions by measuring the extensional wave velocities along these directions, and using the measured velocities in the above Equations (1) to (6) to deduce the Young's moduli. This method and apparatus are applicable to the general case of an anisotropic laminate. It should be noted that the x and y axis directions coincide with the zero-degree and 90-degree fiber directions of the laminate, respectively. Such a coordinate system gives the simplest form of equations for the Young's modulus measurements that practically are most convenient for engineering evaluation. Thus, it will be understood that in order to evaluate the modulus of a plate along the x-axis direction using the equations given above, the sensors must be aligned along the direction corresponding to the zero-degree fiber direction.

In many composite structures, however, quasi-isotropic ply lay-ups are used because-of their advantageous properties. For a quasi-isotropic laminate, the in-plane stiffnesses $A_{11}$ and $A_{22}$ are equal. Accordingly, Equations (1) and (2) indicate that the extensional velocities in the x- and y-directions will be equal, and can be denoted simply as $c_e$. Similarly, Equations (4) and (6) indicate that the Poisson's ratios $v_{xy}$ and $v_{yx}$ will be equal and can be denoted simply as v. The in-plane stiffness $A_{11}$ can be expressed in terms of the extensional velocity $c_e$ by rearranging Equation (1), and the term $A_{22}$ in all of the equations can be replaced by $A_{11}$. From Equation (4), $A_{12}$ can be expressed in terms of $A_{11}$ and Poisson's ratio v. Making the appropriate substitutions, Equations (3) and (5) both reduce to the same equation, $$E=(1-v^2)\rho c_e^2 \qquad (7)$$

Thus, the Young's moduli along the x- or y-directions are equal and can be determined by the processor 22 by measuring the wave velocity along either direction and using Equation (7). Thus, in the case of quasi-isotropic composite laminates, a simplified method and apparatus can be used to deduce stiffness necessitating only a single measurement of wave velocity along any direction in the plane.

Figure 3:
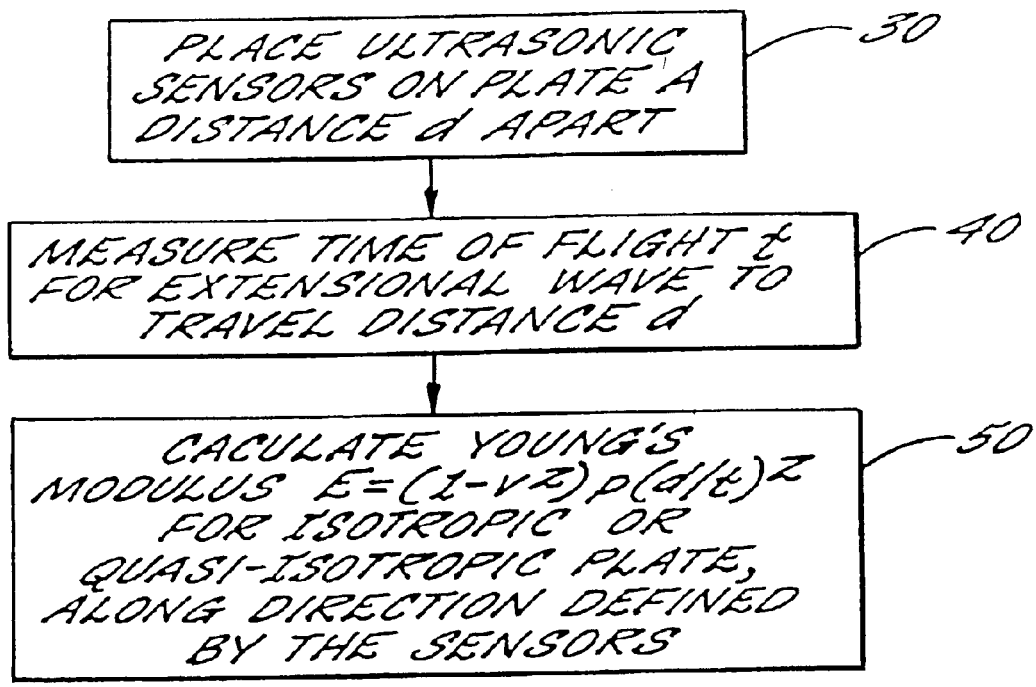
FIG. 3 is a flowchart showing a method for determining Young's modulus of a plate structure in accordance with an embodiment of the invention.

FIG. 3 is a flowchart illustrating a method in accordance with one embodiment of the invention applicable particularly to homogeneous isotropic or quasi-isotropic composite laminate plates. As indicated at 30, suitable acoustic devices such as contact ultrasonic transducers or acoustic emission sensors are placed against the same surface of a plate to be tested such that the sensors are a known distance d apart and are appropriately aligned relative to the fiber directions of the laminate. One of the sensors is activated to emit an acoustical pulse or signal to initiate a plate wave, and the other sensor detects the arrival of the extensional-mode wave component of the plate wave (which travels faster than the flexural-mode component and thus is the first to arrive at the sensor). From the sensor information, a time of flight t is measured by the processor 22 as indicated at 40. Then, at 50, the Young's modulus E for the plate is calculated by the processor based on Equation (7) above, where the wave velocity $c_e$ is equal to d/t.

This method can be further simplified for applications where repeated measurements of the time of flight t are made on a periodic basis, for example, as part of a regular health-monitoring inspection program. In this case, it may be desired only to determine a quantitative change in Young's modulus from one inspection or time to another. If Equation (7) is expressed in terms of time of flight t by substituting d/t for the wave velocity $c_e$, a Young's modulus for an i-th measurement is given by $$E_i = (1-v^2)\rho\left(\frac{d}{t_i}\right)^2 \qquad (8)$$

Consider that at some earlier measurement, an original Young's modulus would have been given by $$E_o = (1-v^2)\rho\left(\frac{d}{t_o}\right)^2 \qquad (9)$$

Next, it is assumed that for each inspection, the sensors are placed the same distance d apart from each other along the same direction. It is further assumed that the density and Poisson's ratio do not change from one inspection to the next. This assumption is considered to be close to reality, inasmuch as the type of material changes of most interest in composite laminates are micro-cracking and other microscopic damage, and thus the changes in Poisson's ratio should be negligible. Accordingly, the ratio of Young's modulus at the i-th measurement to the original Young's modulus is given by $$\frac{E_i}{E_O} = \left(\frac{t_O}{t_i}\right)^2 \quad (10)$$

This can also be expressed in terms of a fractional change as $$\frac{\Delta E}{E_O} = 1 - \left(\frac{t_O}{t_i}\right)^2 \quad (11)$$

Figure 4:
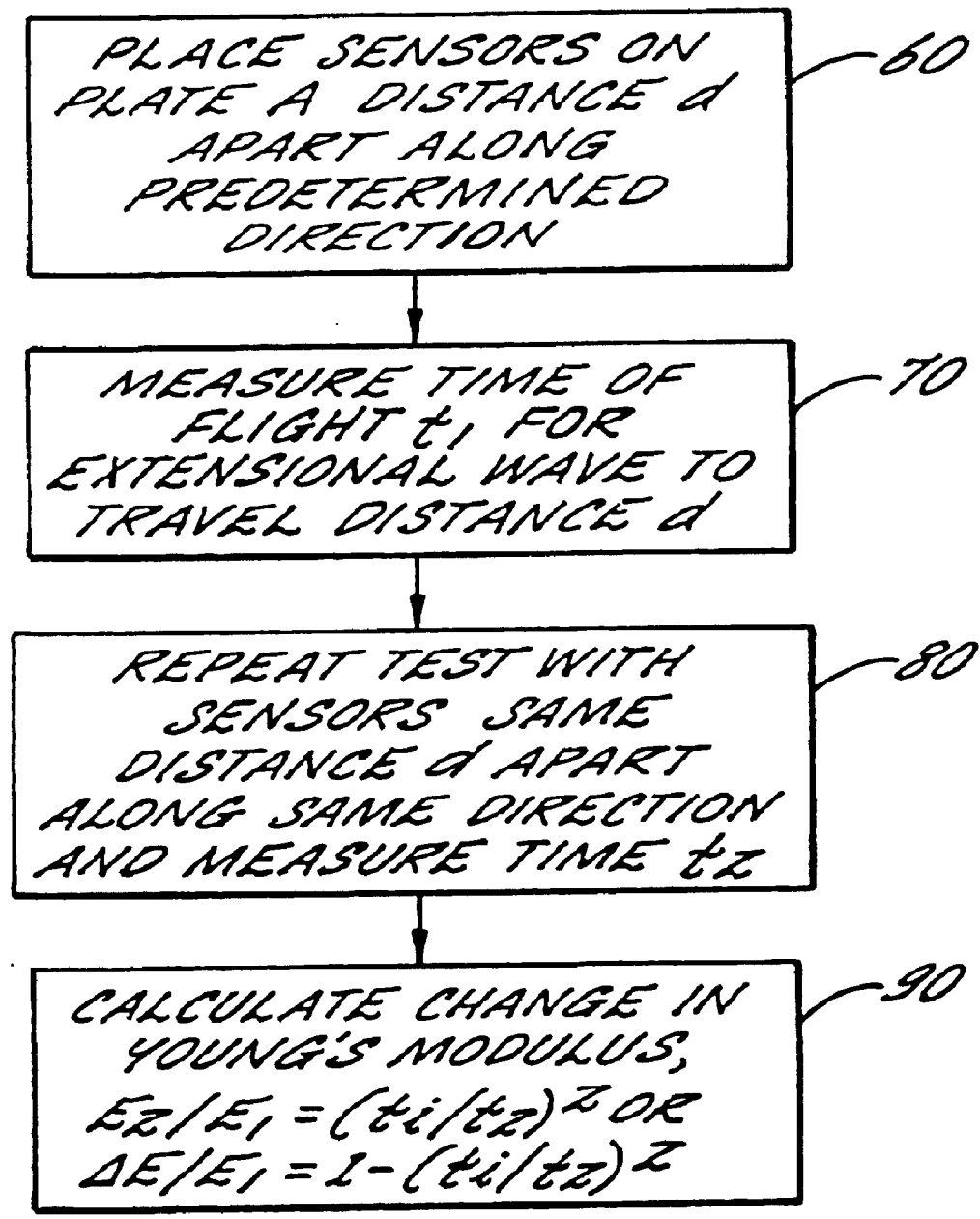
FIG. 4 is a flowchart showing a method for determining a change in Young's modulus of a plate structure in accordance with another embodiment of the invention.

FIG. 4 is a flowchart illustrating a testing sequence based on the Equations (10) and (11). As indicated at 60, sensors are placed on the plate surface a distance d apart from each other along a predetermined direction. At 70, a first test is commenced in which the time of flight $t_1$ of an extensional wave is measured with the sensors. Typically this time of flight $t_1$ is stored in a memory device associated with or included within the processor 22. A second test may subsequently be conducted as indicated at 80, making sure that the sensors are placed the same distance d apart along the same direction as for the prior test, so as to measure a second time of flight $t_2$. At 90, the change in Young's modulus is calculated by the processor using either Equation (10) or (11), or both, based on the ratio of the two times of flight.

From the foregoing, it will be appreciated that the invention provides a method for nondestructively determining quantitative stiffness information for homogeneous and composite laminate plate structures using extensional wave propagation. The method is readily applicable to in-situ inspection because sensors are placed on the same surface of the structure being tested, and therefore it is not necessary to have access to both sides of the plate structure. The sensors advantageously can be permanently bonded on a structure in a critical location for frequent inspection, thereby facilitating testing and also assuring that the sensor spacing and orientation are always fixed in the appropriate manner.

Many modifications and other embodiments of the invention will come to mind to one skilled in the art to which this invention pertains having the benefit of the teachings presented in the foregoing descriptions and the associated drawings. For example, although the foregoing description focuses primarily upon the unique problems associated with evaluating composite laminate plates, the method of the invention is equally applicable to homogeneous isotropic plates, as will be recognized by those skilled in the art. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An apparatus for quantitatively evaluating a material stiffness of a composite laminate plate along an in-plane direction, the plate having a plurality of plies arranged in a balanced symmetric ply lay-up and having opposite major surfaces defining a thickness of the plate therebetween, the apparatus comprising:
   a transducer for initiating an elastic extensional-mode wave that propagates through the plate along said in-plane direction;
   a sensor, spaced apart from said transducer by a distance d, for detecting arrival of the extensional-mode wave; and
   a processor, responsive to said transducer and said sensor, for calculating a material stiffness of the plate along said in-plane direction based on the distance d and an elapsed time between the initiation of the extensional-mode wave by said transducer and the arrival of the extensional-mode wave at said sensor.

2. The apparatus of claim 1, wherein said transducer is in acoustical communication with the plate at a first point located on a first of the major surfaces of the plate so as to cause the extensional-mode wave to originate at said first point and propagate along the plate.

3. The apparatus of claim 2, wherein said sensor is in acoustical communication with the plate at a second point located on said first major surface and spaced in said in-plane direction from the first point by the distance d.

4. The apparatus of claim 3 wherein said processor calculates the material stiffness of the plate along the in-plane direction based on the distance d between the first and second points along said first major surface of the plane in said in-plane direction and the elapsed time t required for the extensional-mode wave to travel the distance d from the first point to the second point.

5. The apparatus of claim 1, wherein the processor calculates the material stiffness by calculating a Young's modulus along said in-plane direction.

6. The apparatus of claim 5, adapted for evaluating a quasi-isotropic composite laminate plate, wherein said processor calculates the Young's modulus E based on the equation $$E = (1-v^2)\rho(d/t)^2,$$

where v is a predetermined Poisson's ratio for the material of the plate and $\rho$ is a predetermined density of the material of the plate.

7. The apparatus of claim 1, wherein said transducer imparts energy to the plate by using acoustic energy to create the extensional-mode wave.

8. The apparatus of claim 7, wherein said transducer is disposed against the first major surface of the plate at the first point and is activated to emit acoustic energy.

9. The apparatus of claim 8, wherein said sensor comprises an acoustic energy detector disposed against the first major surface of the plate at the second point.

10. The apparatus of claim 1 adapted to quantitatively evaluate Young's moduli of the composite laminate plate along two orthogonal in-plane x- and y-directions of the plate, wherein said processor determines a velocity $c_x$ of the extensional wave along said x-direction, determines a velocity $c_y$ of the extensional wave along said y-direction, and determines Young's moduli $E_{xx}$ and $E_{yy}$ respectively along the x- and y-directions by solving a set of simultaneous equations relating the extensional wave velocities, the Young's moduli, and Poisson's ratios and in-plane stiffness parameters for the plate to one another.

11. The apparatus of claim 10, wherein said processor determines the Young's moduli $E_{xx}$ and $E_{yy}$ by solving the set of equations:

$$C_x = \sqrt{A_{11}/\rho h}$$

$$C_y = \sqrt{A_{22}/\rho h}$$

$$E_{xx} = \frac{\sigma_{xx}}{\epsilon_{xx}^\circ} = \frac{A_{11}A_{22} - A_{12}^2}{hA_{22}}$$

$$v_{xy} = -\frac{\epsilon_{yy}^\circ}{\epsilon_{xx}^\circ} = \frac{A_{12}}{A_{22}}$$

-continued $$E_{yy} = \frac{A_{11}A_{22} - A_{12}^2}{hA_{11}}$$

$$v_{yx} = \frac{A_{12}}{A_{11}}$$

where h is a thickness of the plate, $\rho$ is a known density of the plate, and $v_{xy}$ and $v_{yx}$ are known Poisson's ratios for the plate.

12. The apparatus of claim 1 wherein said transducer and said sensor are permanently bonded to the first major surface of the plate.

13. The apparatus of claim 1, wherein said transducer and said sensor are disposed upon a portion of an aircraft that includes the composite laminate plane.

14. An apparatus for quantitatively evaluating a change in Young's modulus of a composite laminate plate along an in-plane direction, the plate having a plurality of plies arranged in a balanced symmetric ply lay-up and having opposite major surfaces defining a thickness of the plate therebetween, the apparatus comprising:
 a transducer for imparting energy to the plate so as to cause extensional-mode waves to originate and propagate along the plate in said in-plane direction;
 a sensor for detecting arrival of a respective extensional-mode wave, said sensor spaced a predetermined distance d in said in-plane direction from said transducer; and
 a processor for determining an elapsed time t required for a respective extensional-mode wave to travel the predetermined distance d during both a first test from which $t_1$ is determined and a subsequent second test from which $t_2$ is determined, and for separately calculating Young's modulus for the plate along said in-plane direction for both the first and second tests, said processor also adapted to calculate a change in Young's modulus for the plate along said in-plane direction based on a degree of difference of the times $t_1$ and $t_2$.

15. The apparatus of claim 14, wherein said transducer and said sensor originate and detect the extensional-mode waves at two different times, whereby the change in Young's modulus represents a change over time.

16. The apparatus of claim 15, wherein said processor calculates the change in Young's modulus based on an assumption that density and Poisson's ratio for the material of the plate are constant between the two different times at which the f extensional-mode waves are originated and detected.

17. The apparatus of claim 14, wherein said processor calculates the change in Young's modulus based upon the Young's modulis calculated for the first test and further based on a ratio of the times $t_1$ and $t_2$.

18. The apparatus of claim 17, wherein said processor calculates the ratio of Young's moduli by the equation $$E_2/E_1 = (t_1/t_2)^2,$$

where $E_1$ is Young's modulus from the first test and $E_2$ is Young's modulus from the second test.

19. The apparatus of claim 14 wherein said transducer and said sensor are disposed upon a first major surface of the plate according to a technique selected from the group consisting of permanently bonding said transducer and said sensor to the first major surface of the plate, embedding said transducer and said sensor in the plate and placing said transducer and said sensor on the first major surface of the plate.

20. The apparatus of claim 14, wherein said transducer and said sensor are disposed upon a portion of an aircraft that includes the composite laminate plane.

* * * * *